United States Patent
Lin et al.

(10) Patent No.: US 7,378,524 B2
(45) Date of Patent: *May 27, 2008

(54) AMINOQUINOLINE COMPOUNDS

(75) Inventors: Chu-Chung Lin, Taichung (TW); Jen-Fuh Liu, Taipei (TW); Chih-Wei Chang, Taipei (TW); Shu-Jen Chen, Taipei (TW); Yibin Xiang, Acton, MA (US); Pei-Chin Cheng, Changhua County (TW); Jiing-Jyh Jan, Taipei County (TW)

(73) Assignee: Taigen Biotechnology Co., Ltd. (TW)

( * ) Notice: Subject to any disclaimer, the term of this patent is extended or adjusted under 35 U.S.C. 154(b) by 543 days.

This patent is subject to a terminal disclaimer.

(21) Appl. No.: 10/953,937

(22) Filed: Sep. 29, 2004

(65) Prior Publication Data
US 2005/0070573 A1    Mar. 31, 2005

Related U.S. Application Data

(63) Continuation-in-part of application No. 10/819,646, filed on Apr. 6, 2004, now Pat. No. 7,183,413.

(60) Provisional application No. 60/551,750, filed on Mar. 9, 2004, provisional application No. 60/462,495, filed on Apr. 11, 2003.

(51) Int. Cl.
  *C07D 215/38* (2006.01)
(52) U.S. Cl. ............... 546/157; 546/153; 546/156
(58) Field of Classification Search .......... 546/153, 546/156, 157
  See application file for complete search history.

(56) References Cited

U.S. PATENT DOCUMENTS

| | | | |
|---|---|---|---|
| 5,756,517 A | 5/1998 | Schohe-Loop et al. | 514/314 |
| 5,866,562 A | 2/1999 | Schohe-Loop et al. | 514/183 |
| 6,174,897 B1 | 1/2001 | Schohe-Loop et al. | 514/312 |
| 6,194,403 B1 | 2/2001 | Hu et al. | 514/213.01 |
| 6,221,882 B1 | 4/2001 | Macfarlane | |
| 6,399,630 B1 | 6/2002 | Macfarlane | |
| 6,521,637 B2 | 2/2003 | Macfarlane | |
| 7,183,413 B2 * | 2/2007 | Lin et al. | 546/157 |

FOREIGN PATENT DOCUMENTS

| | | |
|---|---|---|
| WO | WO 95/23137 | 8/1995 |
| WO | WO 97/21681 | 6/1997 |
| WO | WO 98/55125 | 12/1998 |
| WO | 02/083143 | 10/2002 |

OTHER PUBLICATIONS

Carlier et al., "Heterodimeric Tacrine-Based Acetylcholinesterase Inhibitors: Investigating Ligand-Peripheral Site Interactions", J. Med. Chem. 42:4225-4231, 1999.
Hu et al., "Homodimeric Tacrine Congeners as Acetylcholinesterase Inhibitors", J. Med. Chem. 45:2277-2282, 2002.
Srivastava et al., "Synthesis of Bisquinolines and their In Vitro bility to Produce Methemoglobin In Canine Hemolysate", Bioorganic & Medicinal Chemistry Letters 9:653-658, 1999.

* cited by examiner

*Primary Examiner*—D. Margaret Seaman
(74) *Attorney, Agent, or Firm*—Occhiuti Rohlicek & Tsao LLP

(57) ABSTRACT

This invention relates to treating inflammatory and immune diseases with certain aminoquinoline compounds that bind to CXCR3 receptors. The aminoquinoline compounds are covered by the formula (I) shown below. Each variable is defined in the specification.

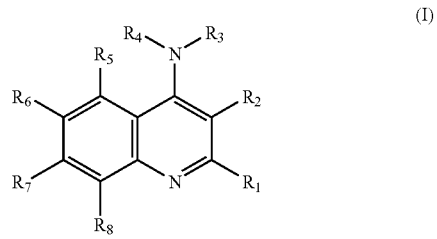

(I)

11 Claims, No Drawings

AMINOQUINOLINE COMPOUNDS

CROSS REFERENCE TO RELATED APPLICATIONS

This application is a continuation-in-part of U.S. Utility application Ser. No. 10/819,646, filed Apr. 6, 2004 now U.S. Pat. No. 7,183,413, which in turn claims priority to U.S. Provisional Application Ser. No. 60/462,495, filed Apr. 11, 2003, and U.S. Provisional Application Ser. No. 60/551,750, filed Mar. 9, 2004. The contents of all parent applications are incorporated herein by reference.

BACKGROUND

Chemokines have been classified into four groups according to their structures. CXC and CC chemokines, the two large groups, feature the presence and absence of an amino acid, respectively, between the first two cysteine residues in a conserved four-cysteine motif (Mackay C. R., Nat. Immunol., (2001) 2:95; Olson et al., Am. J. Physiol. Regul. Integr. Comp. Physiol., (2002) 283:R7). CXCR3 is the first chemokine receptor found to be highly induced by T cell activation (Loetscher et al., J. Exp. Med., (1996) 184:963). CXCR3 is expressed on some circulating blood T cells, B cells, and natural killer cells (Qin et al., J. Clin. Invest., (1998) 101:746). For example, expression of CXCR3 is induced virtually by all T cells in synovial fluid of rheumatoid arthritis and in various inflamed tissues (e.g., ulcerative colitis, chronic vaginitis, and sarcoidosis), particularly in perivascular regions. However, few T cells in normal lymph nodes are induced to express CXCR3 (Agostini et al., J. Immunol., (1998) 161:6413). Expression and responsiveness of CXCR3 can be markedly increased by T cell activation (Rabin et al., J. Immunol., (1999) 162:3840). CXCR3 is also consistently detected in functional forms on transformed B cells obtained from chronic lymphocytic leukemia patients (Trentin et al., J. Clin. Invest., (1999) 104:115).

CXCR3 binds to three highly potent, inflammation-inducible, ELR-negative CXC chemokines, i.e., I-TAC, Mig, and IP-10. These three chemokines chemoattract and induce calcium influx in activated T cells, tumor-infiltrating lymphocytes, and CXCR3-transfected cells (Loetscher et al., Eur. J. Immunol., (1998) 28:3696; Cole et al., J. Exp. Med., (1998) 187:2009; Weng et al., J. Biol. Chem., (1998) 273: 18288). CXCR3 signaling appears to be an important mechanism for selective homing of activated/effector cells, which are known to accumulate preferentially at inflammatory sites and in many tumors. For example, IP-10 is expressed abundantly at various inflammatory sites, particularly those characterized by T cell infiltration, such as in tissues affected by delayed type hypersensitivity responses, experimental autoimmune encephalomyelitis, or a transplant undergoing rejection (Qin et al., J. Clin. Invest., (1998) 101:746). CXCR3 ligand-induced recruitment of leukocytes is thought to be an essential step in the pathogenesis of tissue-specific autoimmune inflammatory diseases, as well as in graft rejection (Hancock et al., J. Exp. Med., (2000) 192:1515).

SUMMARY

This invention is based on the discovery that certain aminoquinoline compounds are effective in treating inflammatory and immune diseases through their binding to CXCR3 receptors.

In one aspect, this invention features aminoquinoline compounds of formula (I) or their salts:

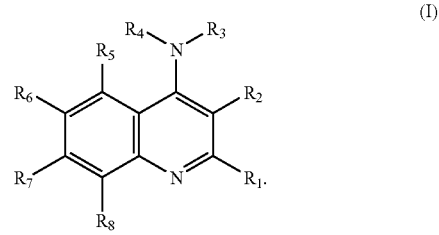

(I)

In this formula, each of $R_1$ and $R_2$, independently, is H or $C_1$-$C_8$ alkyl; each of $R_3$ and $R_4$, independently, is H or -A-N(B)-D; at most one of $R_3$ and $R_4$ being H; and each of $R_5$, $R_6$, $R_7$, and $R_8$, independently, is H, $C_1$-$C_8$ alkyl, or halogen; in which A is $C_1$-$C_{12}$ alkyl optionally containing 1-6 heteroatoms; B is H or $C_1$-$C_8$ alkyl; and D is $C_1$-$C_8$ alkyl, $C_3$-$C_8$ cycloalkyl, $C_3$-$C_8$ heterocycloalkyl, aryl, heteroaryl, —C(O)$R_a$, $SO_2R_a$, —C(=N—CN)—$SR_a$, —C(=N—CN)—$NR_aR_a'$, or —C(=N—C(O)NH$_2$)—$SR_a$; or B and D together are heterocycloalkyl or heteroaryl; each of $R_a$ and $R_a'$, independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl.

Referring to formula (I), a subset of the compounds described above are those in which A is $C_1$-$C_{12}$ alkylcarbonyl containing 1-6 heteroatoms and substituted with arylsulfonyl and D is $C_1$-$C_8$ alkyl, heteroaryl, or aryl optionally substituted with $C_1$-$C_8$ alkyl, heteroaryl, —NO$_2$, —$OR_b$, —N($R_b$)—C(O)$R_b'$, —$NR_bR_b'$, —$CO_2R_b$, —C(O)—$NR_bR_b'$, —C(O)$R_b$, —SO$_2$—$NR_bR_b'$, or —SO$_2R_b$; or D and B together are $C_5$-$C_7$ heterocycloalkyl; each of $R_b$ and $R_b'$, independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl.

The term "alkyl" refers to a saturated, linear or branched hydrocarbon moiety, such as —CH$_3$, —CH$_2$—, or branched —C$_3$H$_7$. The term "alkenyl" refers to a linear or branched, non-aromatic hydrocarbon moiety having at least one double bond, such as —CH=CH$_2$ or —CH=CH—. The term "alkynyl" refers to a linear or branched, non-aromatic hydrocarbon moiety having at least one triple bond, such as —C≡CH or —C≡C—. Alkyl, alkenyl, and alkynyl may optionally contain heteroatoms, such as —(CH$_2$)$_2$N(CH$_2$)$_2$— or —(CH$_2$)$_2$N(CH$_2$)$_2$C(O)—. The term "cycloalkyl" refers to a saturated cyclic hydrocarbon moiety, such as cyclohexyl. The term "cycloalkenyl" refers to a non-aromatic cyclic hydrocarbon moiety having at least one double bond in the ring, such as 2-cyclopentenyl. The term "heterocycloalkyl" refers to a saturated non-aromatic cyclic moiety having at least one ring heteroatom (e.g., O, N, and S), such as 4-tetrahydropyranyl. The term "heterocycloalkenyl" refers to a non-aromatic cyclic moiety having at least one ring heteroatom and at least one double bond in the ring, such as 3,4-dihydropyran-4-yl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Examples of substituents for cycloalkyl, cycloalkenyl, heterocycloalkyl, heterocycloalkenyl, aryloxy, heteroaryloxy, aryl, and heteroaryl include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, $C_1$-$C_{10}$ alkylsulfonyl, arylsulfonyl, heteroarylsulfonyl, amino, $C_1$-$C_{10}$ alkylamino, $C_1$-$C_{20}$ dialkylamino, arylamino, diarylamino, $C_1$-$C_{10}$ alkylimino, arylimino, amido, carbamoyl, thioamido, thiocarbamoyl, hydroxyl, halogen, thio, $C_1$-$C_{10}$ alkylthio, arylthio, cyano, nitro, acyl, acyloxy, carboxyl, and carboxylic ester. Examples of substituents for alkyl, alkenyl, alkynyl, and alkoxy include all of the above substitutents except $C_1$-$C_{10}$ alkyl, $C_2$-$C_{10}$ alkenyl, and $C_2$-$C_{10}$ alkynyl. Cycloalkyl, cycloalkenyl, heterocycloalkyl heterocycloalkenyl, aryl, and heteroaryl also include fused groups.

In another aspect, this invention features aminoquinoline compounds of formula (I) shown above except that each of $R_1$ and $R_2$, independently, is H or $C_1$-$C_8$ alkyl; or $R_1$ and $R_2$ together are $C_5$-$C_8$ cycloalkyl; and one of $R_5$, $R_6$, $R_7$, and $R_8$ is $C_1$-$C_8$ alkyl; the other of $R_5$, $R_6$, $R_7$, and $R_8$, independently, is H, $C_1$-$C_8$ alkyl, or halogen.

In still another aspect, this invention features a method for treating an inflammatory or immune disease. The method includes administering to a subject in need of treatment of an effective amount of one or more compounds of formula (I) shown above except that each of $R_1$ and $R_2$, independently, is H or $C_1$-$C_8$ alkyl; or $R_1$ and $R_2$ together are $C_5$-$C_8$ cycloalkyl; and each of $R_5$, $R_6$, $R_7$, and $R_8$, independently, is H, $C_1$-$C_8$ alkyl, or halogen.

"Treatment" refers to administering one or more aminoquinoline compounds to a subject, who has an inflammatory or immune disease, a symptom of such a disease, or a predisposition toward such a disease, with the purpose to confer a therapeutic effect, e.g., to cure, relieve, alter, affect, ameliorate, or prevent the inflammatory or immune disease, the symptom of it, or the predisposition toward it. "An effective amount" refers to the amount of one or more active aminoquinoline compounds that is required to confer a therapeutic effect on a treated subject.

An inflammatory disease is characterized by a local or systemic, acute or chronic inflammation. An immune disease is characterized by a hyper- or hypo-reaction of the immune system. Examples of inflammatory or immune diseases include neurodegenerative disease (e.g., Alzheimer's disease), multiple sclerosis, systemic lupus erythematosus, rheumatoid arthritis, ankylosing spondylitis, psoriatic arthritis, juvenile rheumatoid arthritis, atherosclerosis, vasculitis, chronic heart failure, cerebrovascular ischemia, encephalitis, meningitis, hepatitis, nephritis, sepsis, sarcoidosis, psoriasis, eczema, uticaria, type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, pulmonary fibrosis, endometriosis, gout, cancer, cachexia, a viral infection, a bacterial infection, an organ transplant condition, a skin transplant condition, or a graft versus host disease.

A subject in need of treatment of an inflammatory or immune disease can also be concurrently administered with an aminoquinoline compound described above and one or more other therapeutic agents at the same time or at different times during the period of treatment. Examples of such a therapeutic agent include an anti-inflammatory agent, a COX2 inhibitor, a leukotriene receptor inhibitor, a prostaglandin modulator, a TNF modulator, or an immunosuppressive agent (e.g., cyclosporine A).

In a further aspect, this invention features a pharmaceutical composition that contains an effective amount of at least one of the above-mentioned aminoquinoline compounds and a pharmaceutically acceptable carrier.

The aminoquinoline compounds described above include the compounds themselves, as well as their salts, prodrugs, and solvates, if applicable. A salt, for example, can be formed between an anion and a positively charged group (e.g., amino) on an aminoquinoline compound. Suitable anions include chloride, bromide, iodide, sulfate, bisulfate, sulfamate, nitrate, phosphate, citrate, methanesulfonate, trifluoroacetate, maleate, succinate, fumarate, tartrate, salicylate, lactate, naphthalenesulfonate, and acetate. Likewise, a salt can also be formed between a cation and a negatively charged group (e.g., carboxylate) on an aminoquinoline compound. Suitable cations include sodium ion, potassium ion, magnesium ion, calcium ion, and an ammonium cation such as tetramethylammonium ion. The aminoquinoline compounds also include those salts containing quaternary nitrogen atoms. Examples of prodrugs include esters and other pharmaceutically acceptable derivatives, which, upon administration to a subject, are capable of providing active aminoquinoline compounds. A solvate refers to a complex formed between an aminoquinoline compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the aminoquinoline compounds described above for use in treating an inflammatory disease or an immune disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary compounds, compounds 1-90, of this invention.

Compound 1

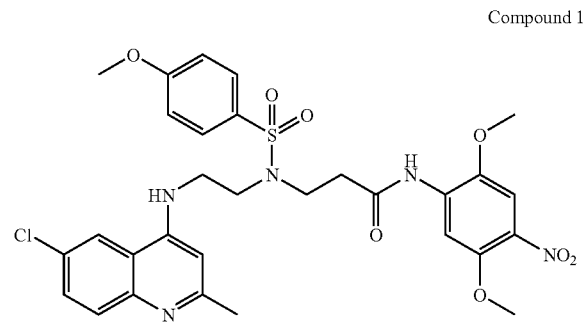

-continued
Compound 2
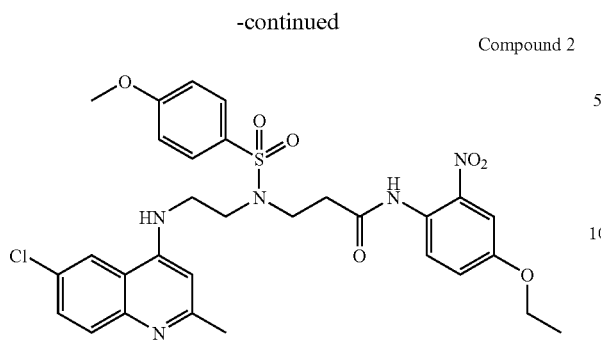
Compound 3
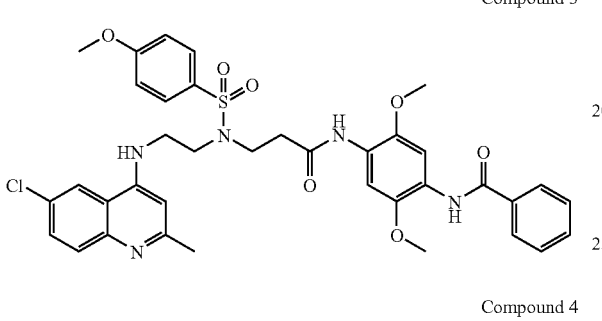
Compound 4
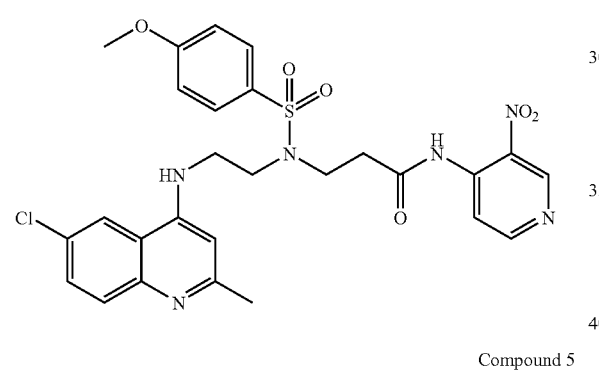
Compound 5
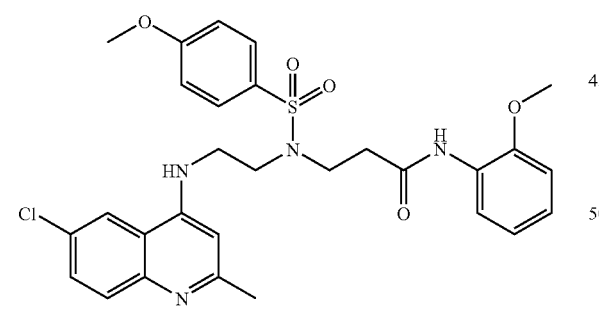
Compound 6
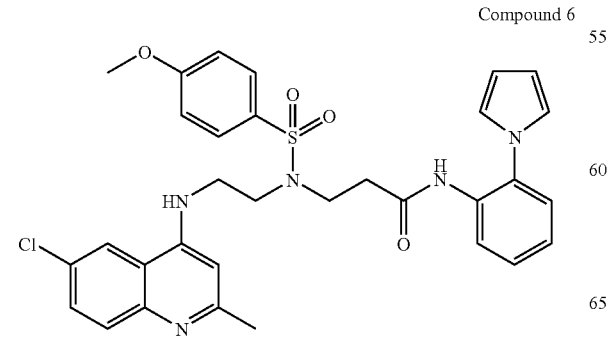
-continued
Compound 7
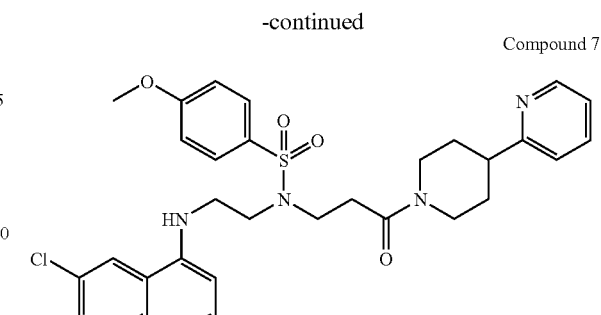
Compound 8
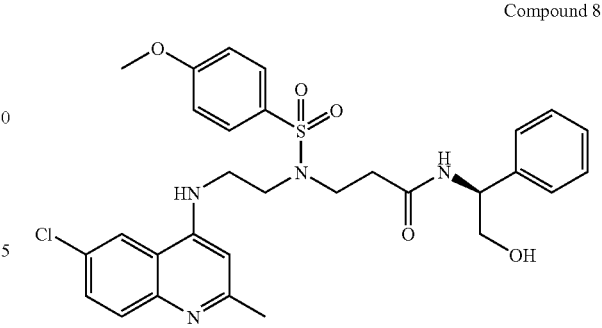
Compound 9
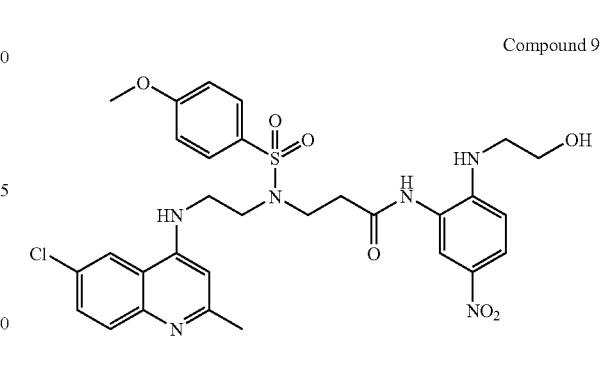
Compound 10
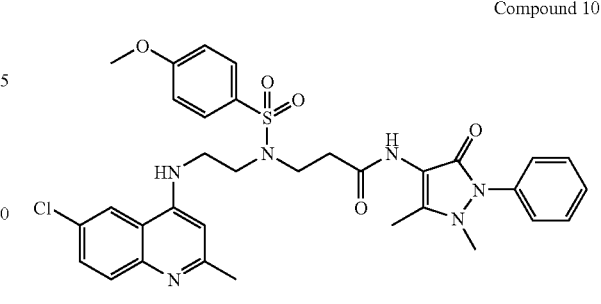
Compound 11

Compound 12
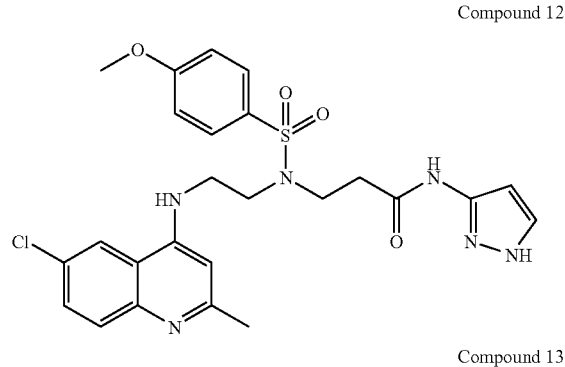
Compound 13
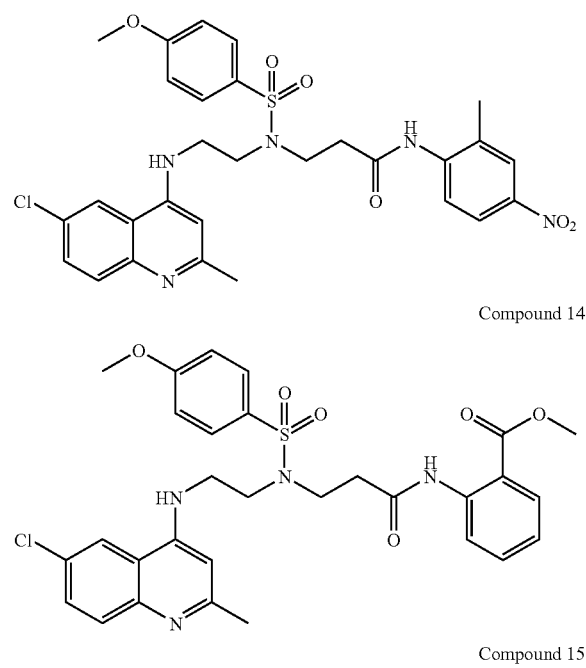
Compound 14
Compound 15
Compound 16
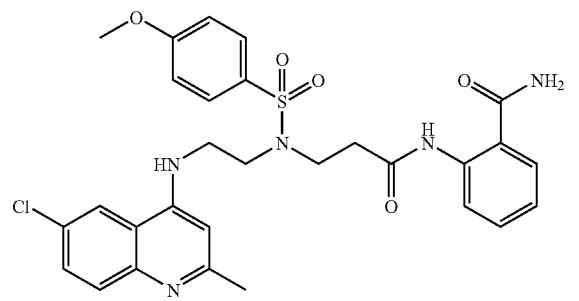
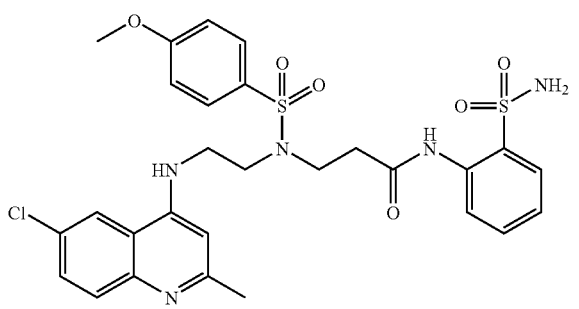
Compound 17
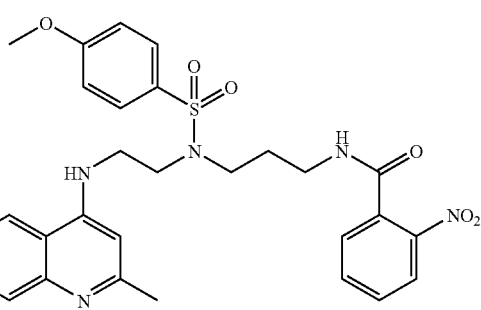
Compound 18
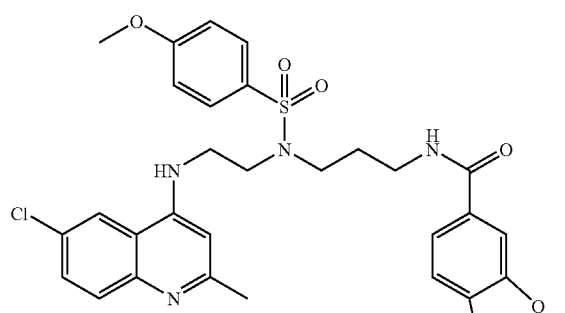
Compound 19
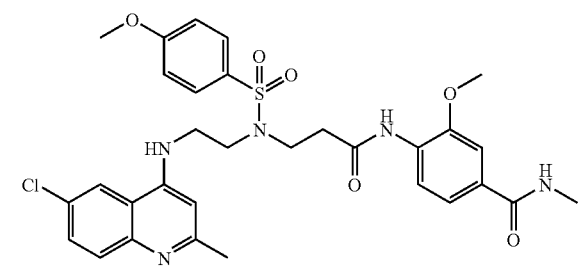
Compound 20
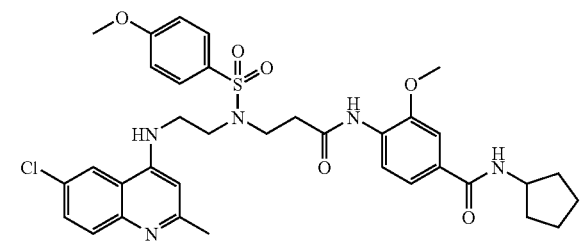
Compound 21
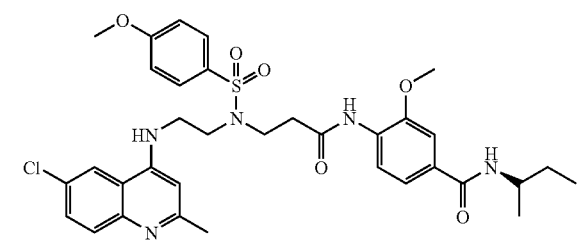

Compound 22
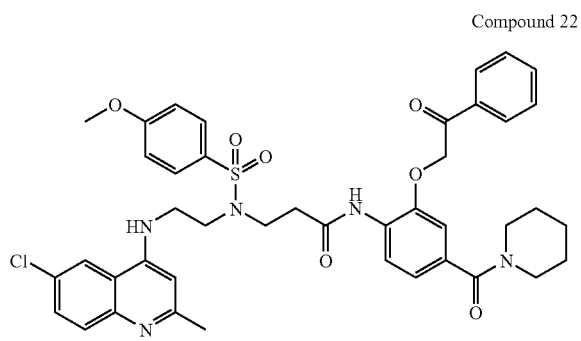
Compound 23
Compound 24
Compound 25
Compound 26
Compound 27
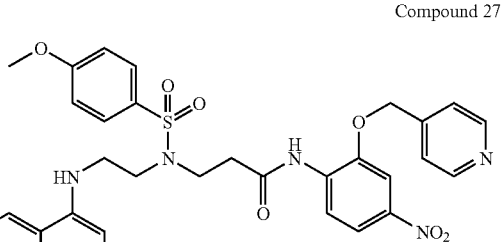
Compound 28
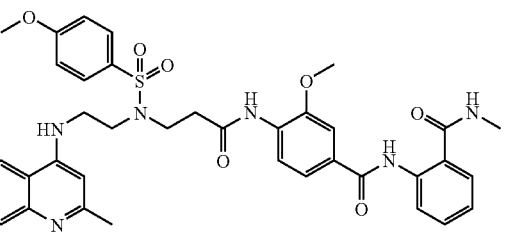
Compound 29
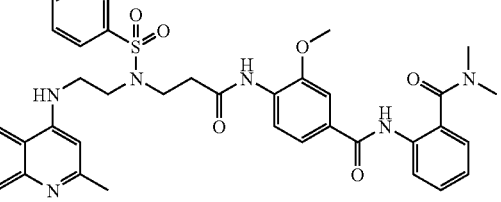
Compound 30
Compound 31
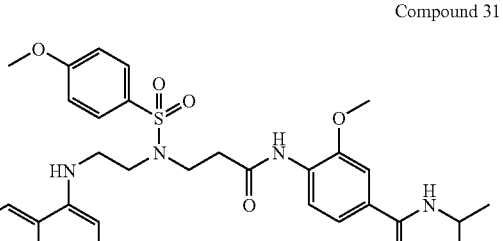
Compound 32
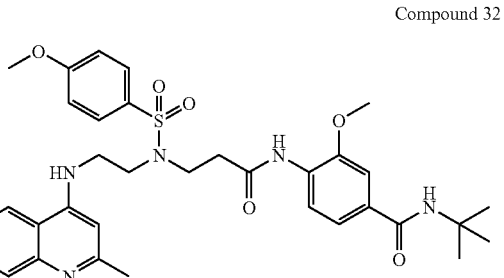

Compound 33
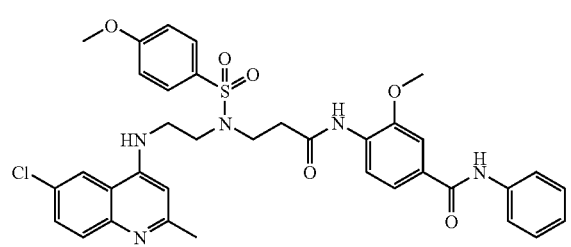
Compound 34
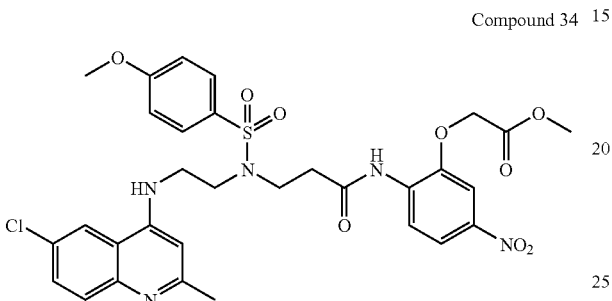
Compound 35
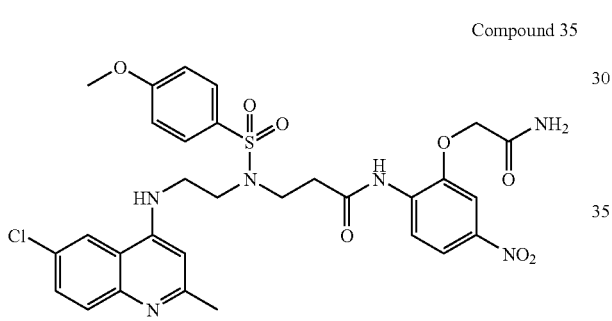
Compound 36
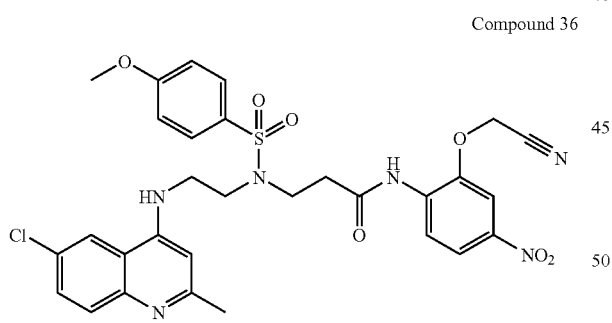
Compound 37
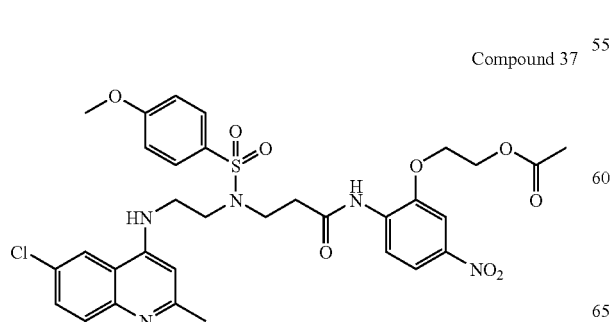
Compound 38
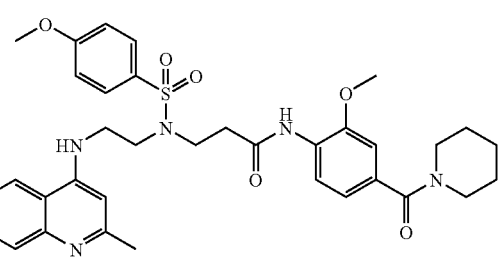
Compound 39
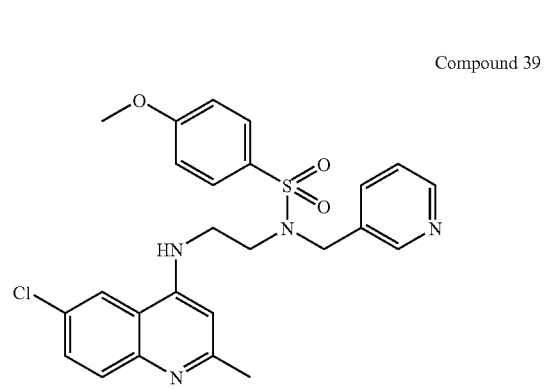
Compound 40
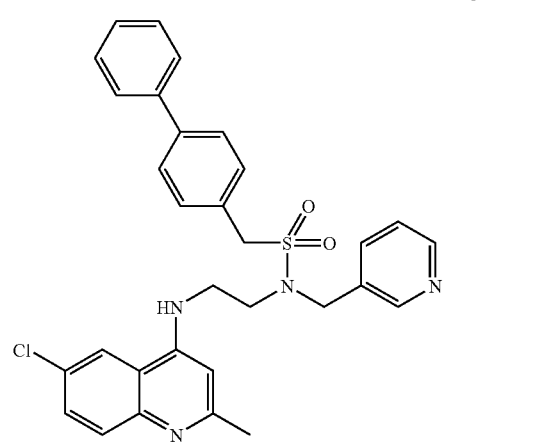
Compound 41
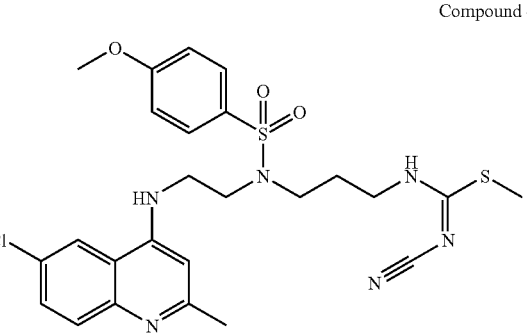

Compound 42
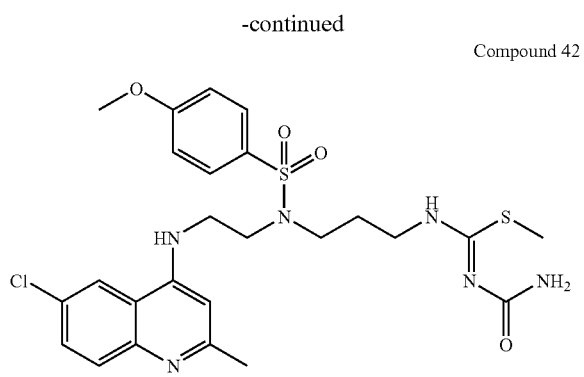
Compound 43
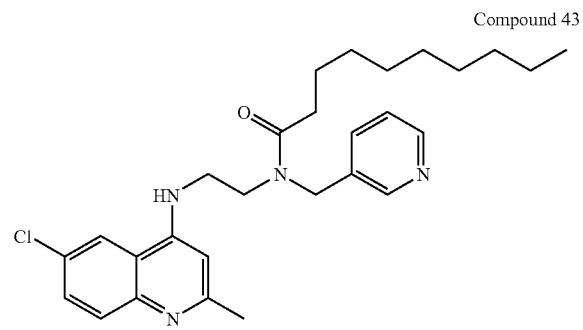
Compound 44
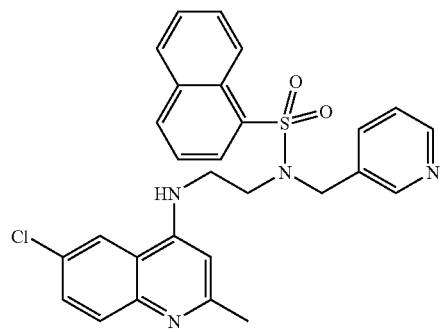
Compound 45
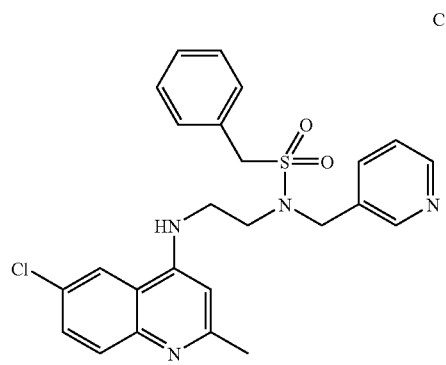
Compound 46
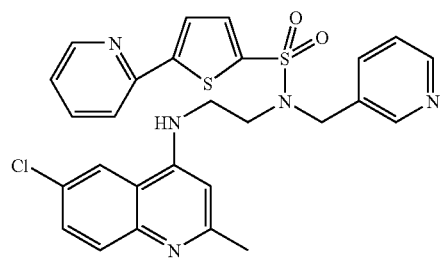
Compound 47
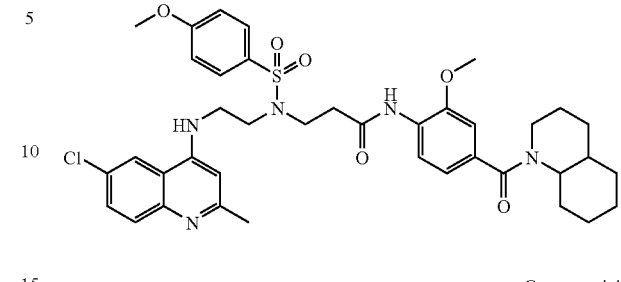
Compound 48
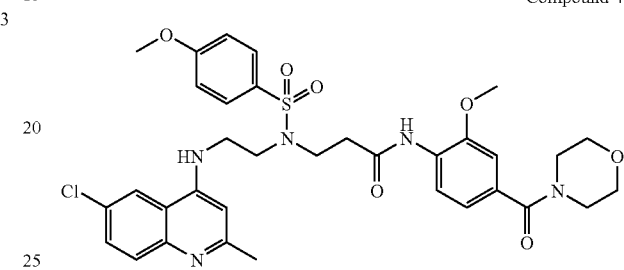
Compound 49
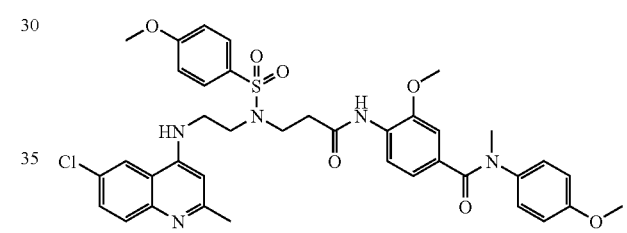
Compound 50
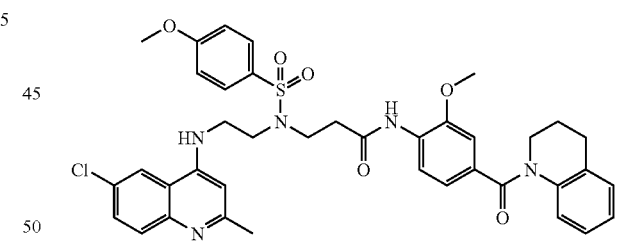
Compound 51
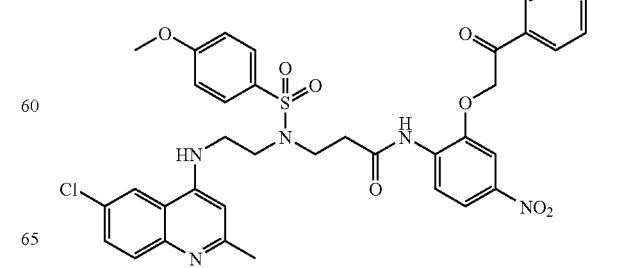

Compound 52
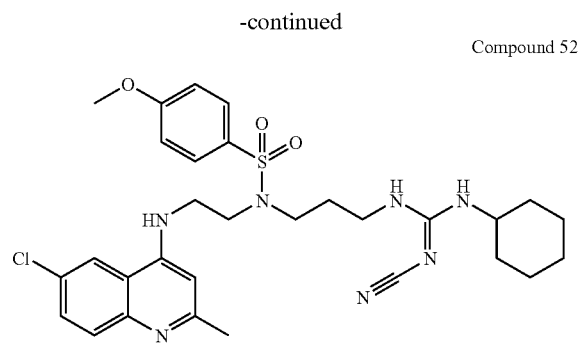
Compound 53
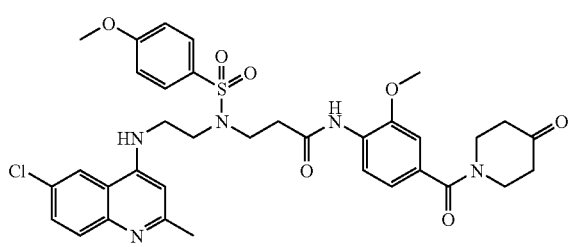
Compound 54
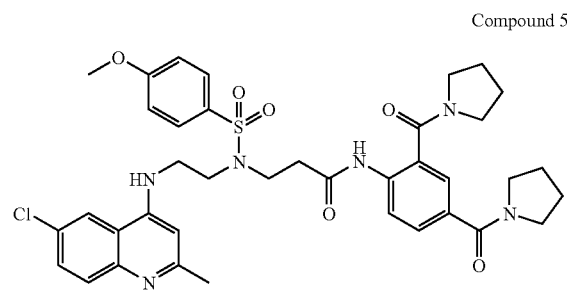
Compound 55
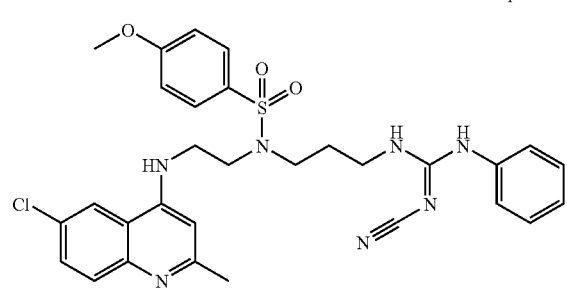
Compound 56
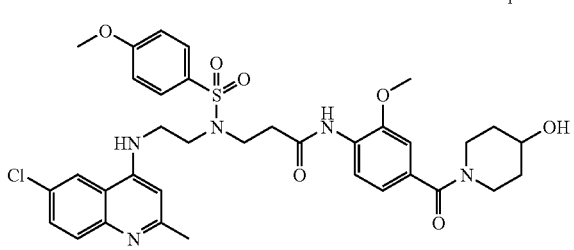
Compound 57
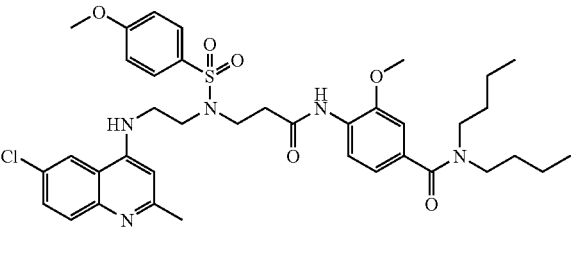
Compound 58
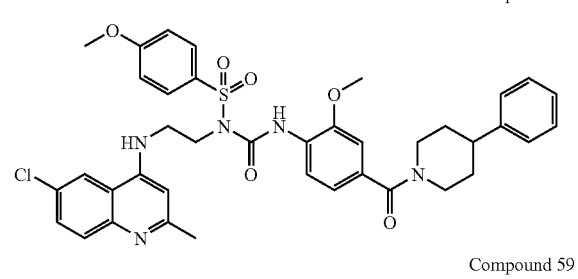
Compound 59
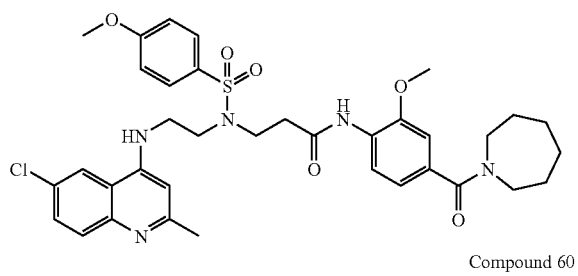
Compound 60
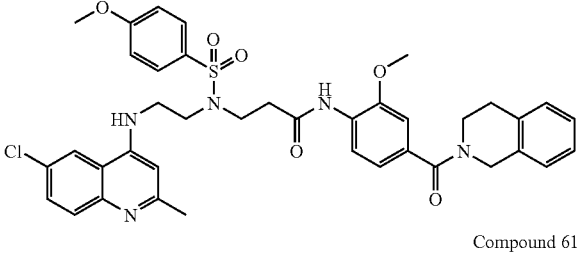
Compound 61
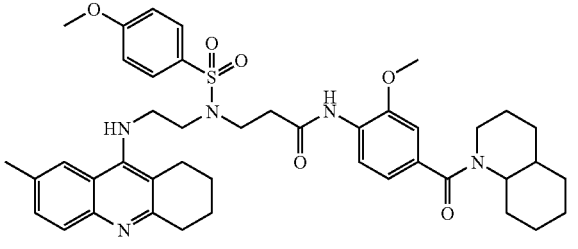
Compound 62

Compound 63
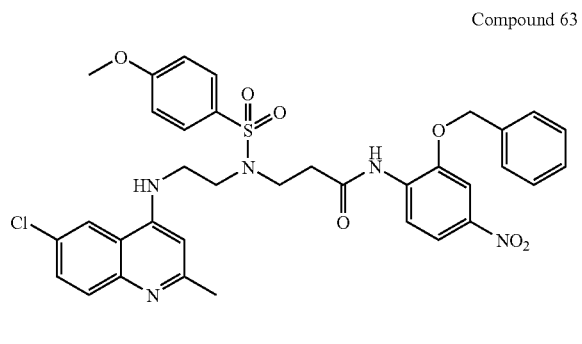
Compound 64
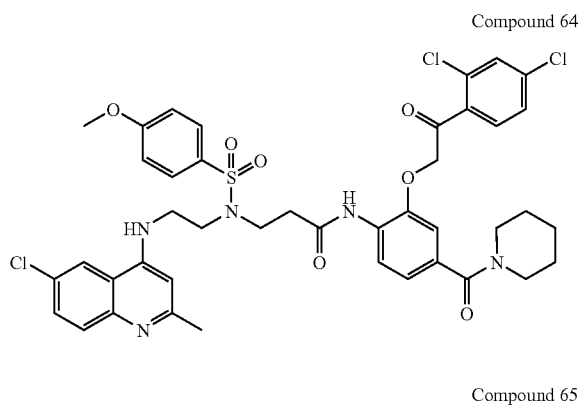
Compound 65
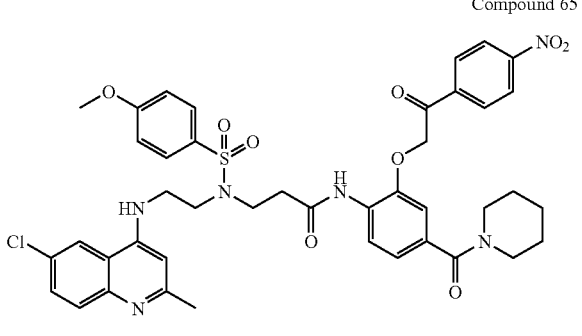
Compound 66
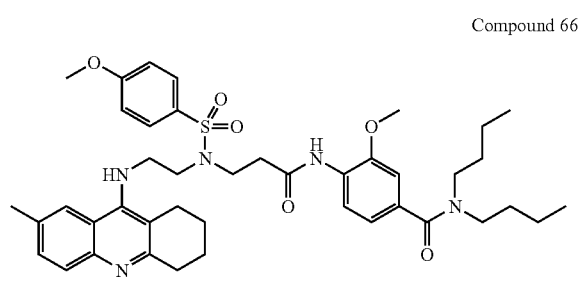
Compound 67
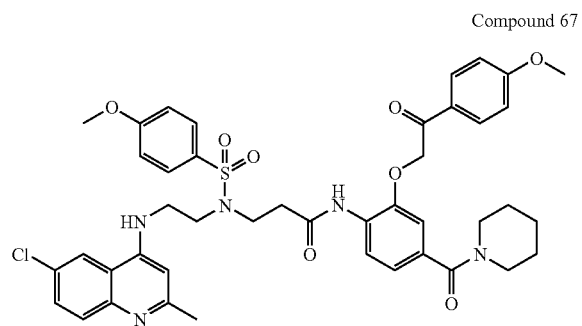
Compound 68
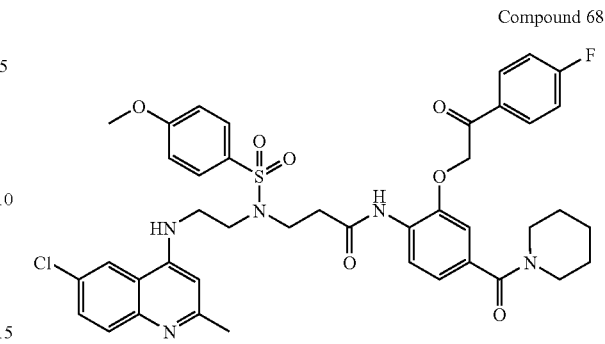
Compound 69
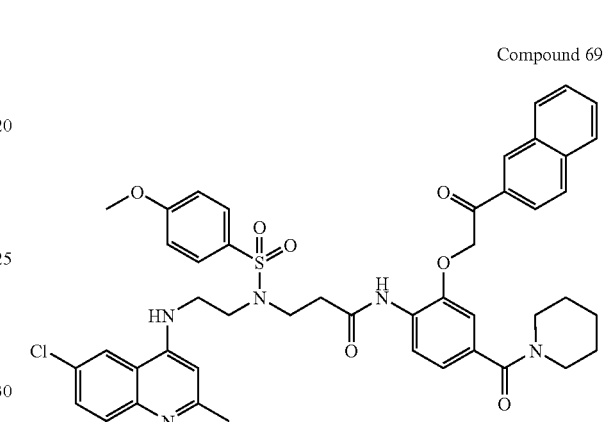
Compound 70
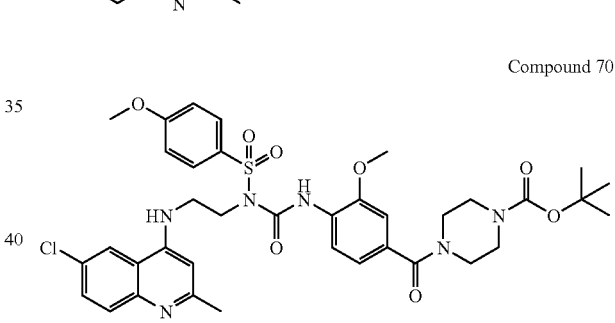
Compound 71
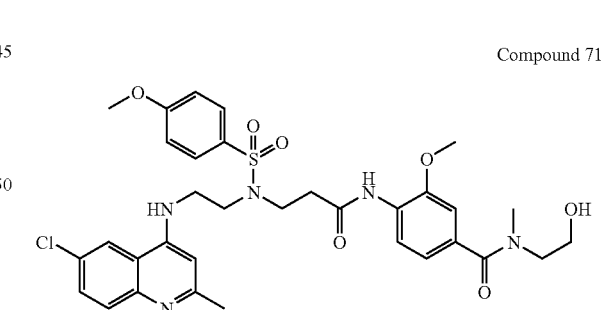
Compound 72
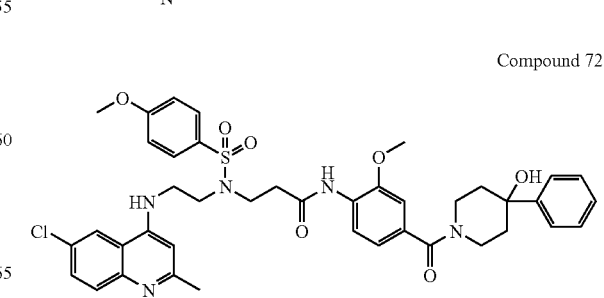

-continued
Compound 73
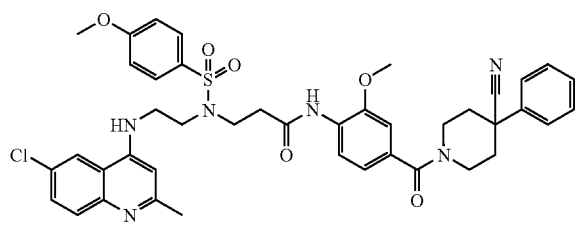
Compound 78
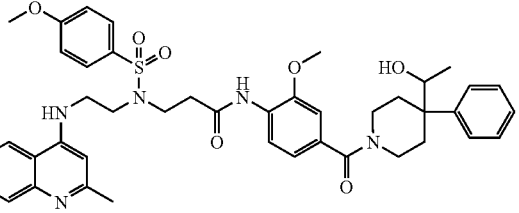
Compound 74
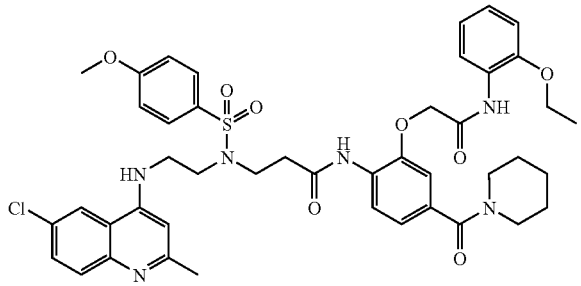
Compound 79
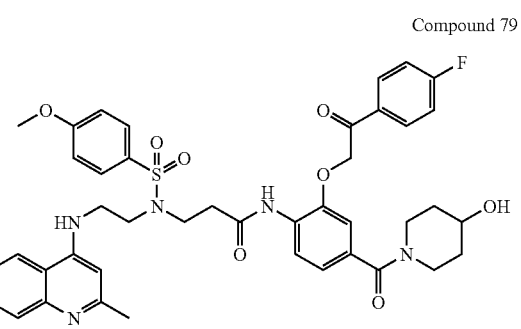
Compound 75
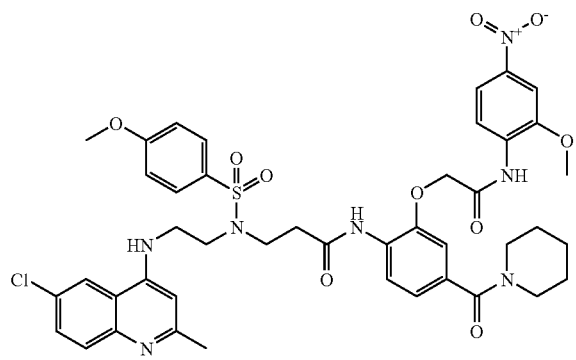
Compound 80
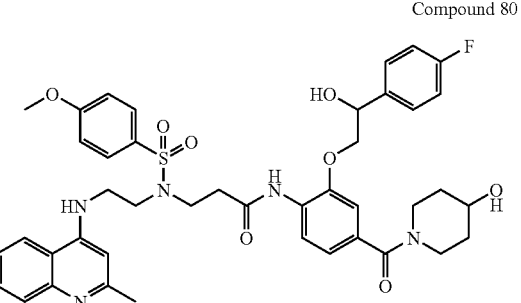
Compound 76
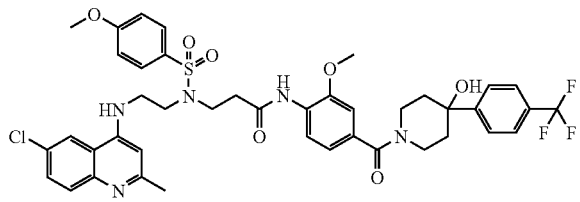
Compound 81
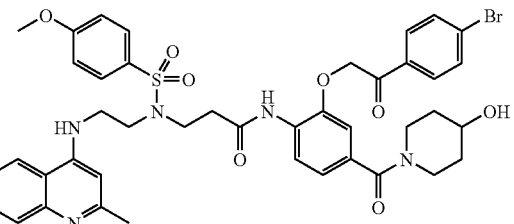
Compound 77
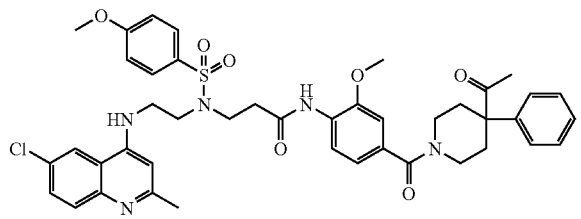
Compound 82
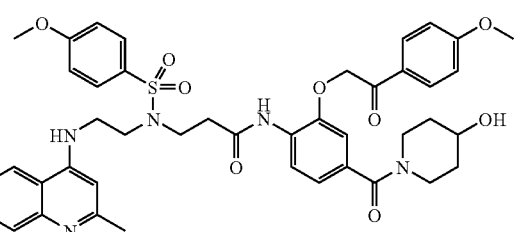

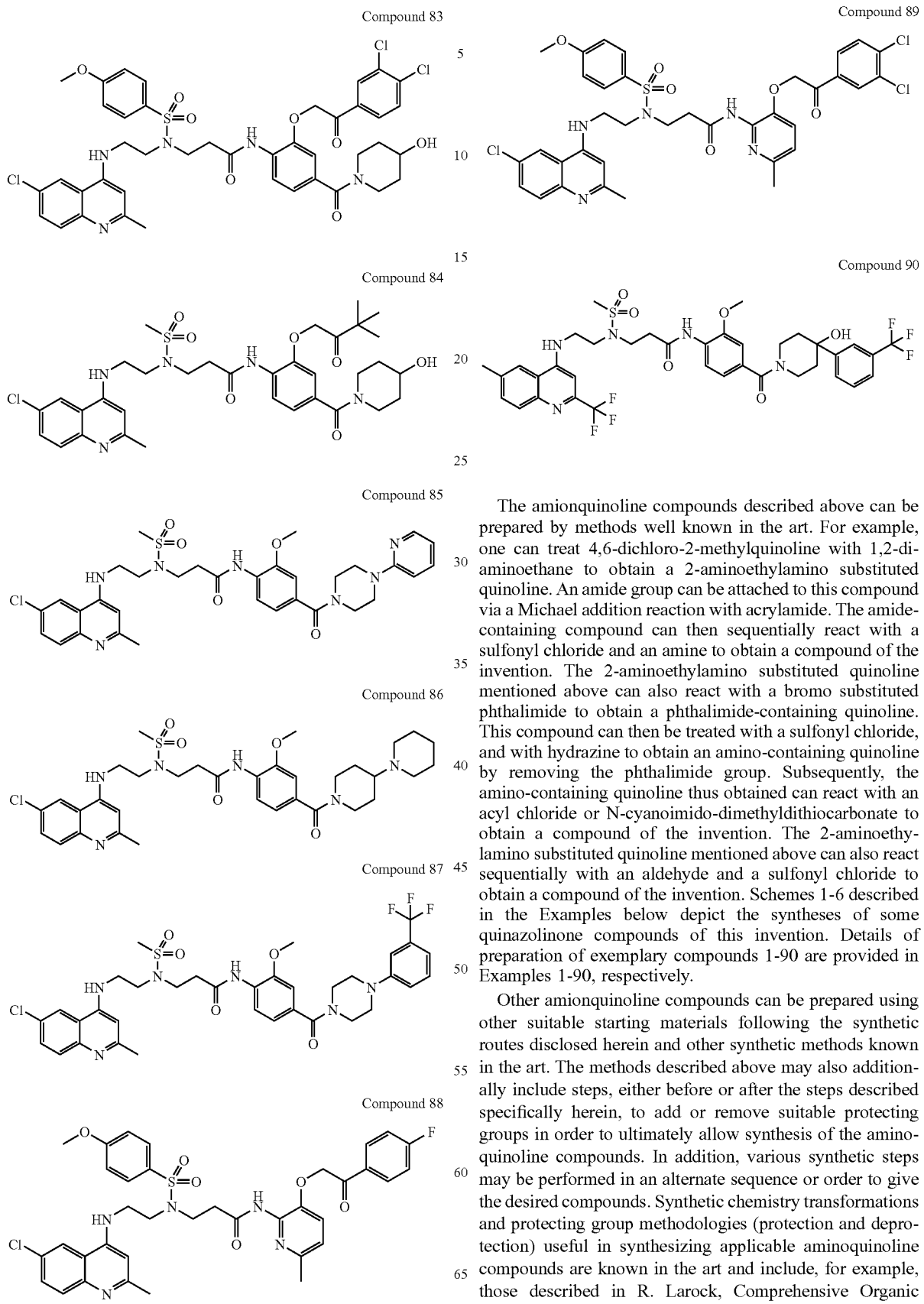

The amionquinoline compounds described above can be prepared by methods well known in the art. For example, one can treat 4,6-dichloro-2-methylquinoline with 1,2-diaminoethane to obtain a 2-aminoethylamino substituted quinoline. An amide group can be attached to this compound via a Michael addition reaction with acrylamide. The amide-containing compound can then sequentially react with a sulfonyl chloride and an amine to obtain a compound of the invention. The 2-aminoethylamino substituted quinoline mentioned above can also react with a bromo substituted phthalimide to obtain a phthalimide-containing quinoline. This compound can then be treated with a sulfonyl chloride, and with hydrazine to obtain an amino-containing quinoline by removing the phthalimide group. Subsequently, the amino-containing quinoline thus obtained can react with an acyl chloride or N-cyanoimido-dimethyldithiocarbonate to obtain a compound of the invention. The 2-aminoethylamino substituted quinoline mentioned above can also react sequentially with an aldehyde and a sulfonyl chloride to obtain a compound of the invention. Schemes 1-6 described in the Examples below depict the syntheses of some quinazolinone compounds of this invention. Details of preparation of exemplary compounds 1-90 are provided in Examples 1-90, respectively.

Other amionquinoline compounds can be prepared using other suitable starting materials following the synthetic routes disclosed herein and other synthetic methods known in the art. The methods described above may also additionally include steps, either before or after the steps described specifically herein, to add or remove suitable protecting groups in order to ultimately allow synthesis of the aminoquinoline compounds. In addition, various synthetic steps may be performed in an alternate sequence or order to give the desired compounds. Synthetic chemistry transformations and protecting group methodologies (protection and deprotection) useful in synthesizing applicable aminoquinoline compounds are known in the art and include, for example, those described in R. Larock, Comprehensive Organic Transformations, VCH Publishers (1989); T. W. Greene and P. G. M. Wuts, Protective Groups in Organic Synthesis, 2nd Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The aminoquinoline compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one aminoquinoline compound described above and a pharmaceutical acceptable carrier. Further, this invention covers a method of administering an effective amount of one or more of the aminoquinoline compounds to a patient with an inflammatory or immune disease. Effective doses will vary, as recognized by those skilled in the art, depending on the types of diseases treated, route of administration, excipient usage, and the possibility of co-usage with other therapeutic treatment.

To practice the method of the present invention, a composition having one or more aminoquinoline compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active aminoquinoline compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active aminoquinoline compound. Examples of other carriers include colloidal silicon oxide, magnesium stearate, cellulose, sodium lauryl sulfate, and D&C Yellow # 10.

The aminoquinoline compounds of this invention can be preliminarily screened for their efficacy in treating inflammatory or immune diseases by an in vitro assay (See Example 91 below) and then confirmed by animal experiments and clinical trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Compound 1 was prepared following the procedures described below:

Scheme 1

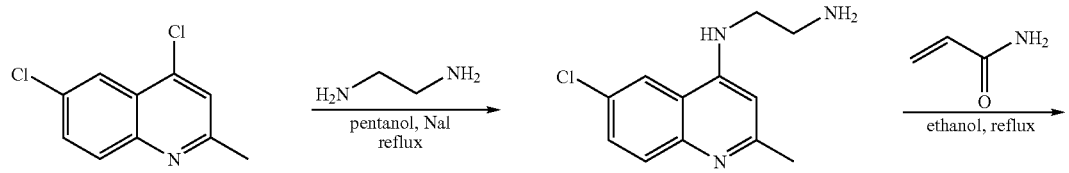

I

-continued

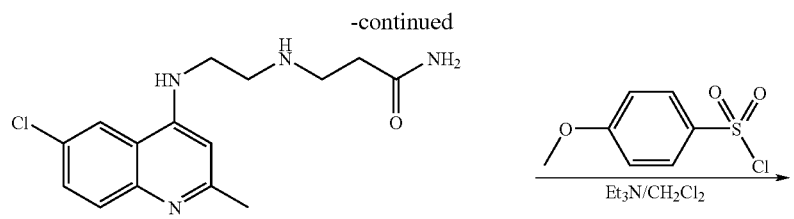

II

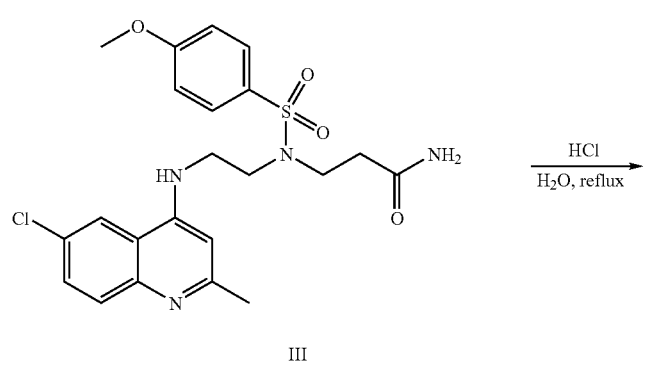

III

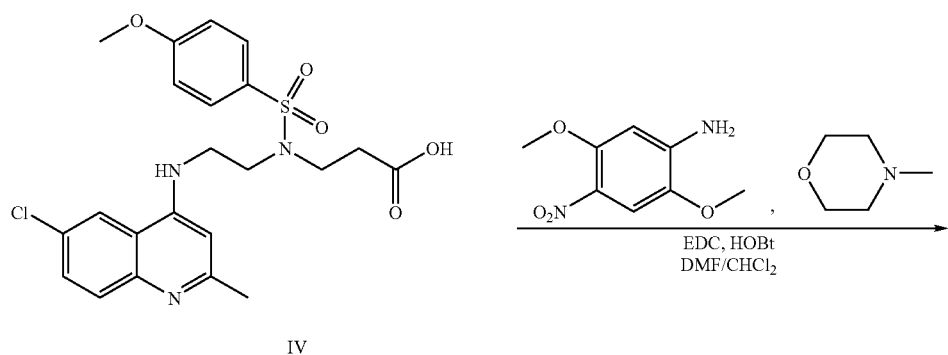

IV

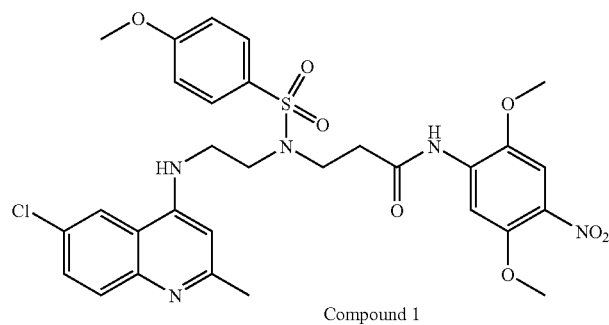

Compound 1

Ethane-1,2-diamine (18 g, 300.0 mmol) was added to a solution of 4,6-dichloro-2-methyl-quinoline (21.2 g, 100.0 mmol) and NaI (in an excess amount) in n-pentanol (80 mL) at room temperature. The reaction mixture was kept under reflux for 12 hours, and then the solvent was removed under vacuum. The residue thus obtained was washed with water and dried under vacuum to afford 28.2 g of Intermediate I as a white solid.

Intermiedate I (23.5 g, 100.0 mmol) and acrylamide (7.8 g, 110 mmol) were suspended in ethanol (200 mL). The mixture was kept under reflux for 8 hours and then was cooled down to room temperature. The reaction solvent was removed under vacuum. The crude product thus obtained was purified by re-crystallization from water to afford 25.6 g of Intermediate II as a white powder.

Triethylamine (15 mL) was added dropwise to a solution of intermediate II (30.6 g, 100 mmol) and 4-methoxy-benzenesulfonyl chloride (24.8 g, 120 mmol) in dichloromethane (220 mL) via an addition funnel over 30 minutes at 0° C. After the addition was complete, the reaction was stirred for 2 hours. The reaction was then quenched with 1 N NaOH and extracted with dichloromethane. The organic extract was dried over magnesium sulfate, filtered, and concentrated under vacuum. The crude product thus obtained was purified by re-crystallization from ethanol to afford 45.2 g of Intermediate III.

HCl (3.0 N, 30 mL) was added to a solution of intermediate III (4.7 g, 10.0 mmol) in $H_2O$ (80 mL). The reaction mixture was refluxed for 10 hours and then was cooled down to room temperature. The product was precipitated and filtered to afford 3.9 g of Intermediate 1V.

N-methylmorpholine (0.2 g, 2.0 mmol) was added to a solution of intermediate IV (0.48 g, 1.0 mmol), 1-ethyl-3-(3-dimethylaminopropyl)-carbodiimide (EDC, 0.3 g, 1.5 mmol), 1-hydroxybenzotriazole (HOBt, in a catalytic amount), and 2,5-dimethoxy-4-nitro-phenylamine (0.2 g, 1.0 mmol) in DMF (10 mL) and dichloromethane (10 mL). The reaction mixture was stirred at room temperature overnight. It was then diluted with dichloromethane (40 mL) and washed with saturated sodium bicarbonate solutions (2×30 mL). The organic layer was dried over magnesium sulfate, filtered, and concentrated under vacuum. The crude product thus obtained was purified by column chromatography over silica gel to afford 0.5 g of Compound 1.

LC/MS $(M+1)^+$: 658.1.

EXAMPLE 2

Compound 2 was prepared in a manner similar to that described in Example 1.

LC/MS $(M+1)^+$: 642.1.

EXAMPLE 3

Compound 3 was prepared in a manner similar to that described in Example 1.

LC/MS $(M+1)^+$: 731.9.

EXAMPLE 4

Compound 4 was prepared in a manner similar to that described in Example 1.

LC/MS $(M+1)^+$: 599.

EXAMPLE 5

Compound 5 was prepared in a manner similar to that described in Example 1.

LC/MS $(M+1)^+$: 582.9.

EXAMPLE 6

Compound 6 was prepared in a manner similar to that described in Example 1.

LC/MS $(M+1)^+$: 617.9.

EXAMPLE 7

Compound 7 was prepared in a manner similar to that described in Example 1.

LC/MS $(M+1)^+$: 622.9.

EXAMPLE 8

Compound 8 was prepared in a manner similar to that described in Example 1.

LC/MS $(M+1)^+$: 596.9.

EXAMPLE 9

Compound 9 was prepared in a manner similar to that described in Example 1.

LC/MS $(M+1)^+$: 656.9.

EXAMPLE 10

Compound 10 was prepared in a manner similar to that described in Example 1.

LC/MS $(M+1)^+$: 663.1.

EXAMPLE 11

Compound 11 was prepared in a manner similar to that described in Example 1.

LC/MS $(M+1)^+$: 592.9.

EXAMPLE 12

Compound 12 was prepared in a manner similar to that described in Example 1.

LC/MS $(M+1)^+$: 543.1.

EXAMPLE 13

Compound 13 was prepared in a manner similar to that described in Example 1.

LC/MS $(M+1)^+$: 611.9.

EXAMPLE 14

Compound 14 was prepared in a manner similar to that described in Example 1.

LC/MS $(M+1)^+$: 610.9.

EXAMPLE 15

Compound 15 was prepared in a manner similar to that described in Example 1.

LC/MS $(M+1)^+$: 595.9.

EXAMPLE 16

Compound 16 was prepared in a manner similar to that described in Example 1.

LC/MS $(M+1)^+$: 632.

EXAMPLE 17
Compound 17 was prepared following the procedures described below:
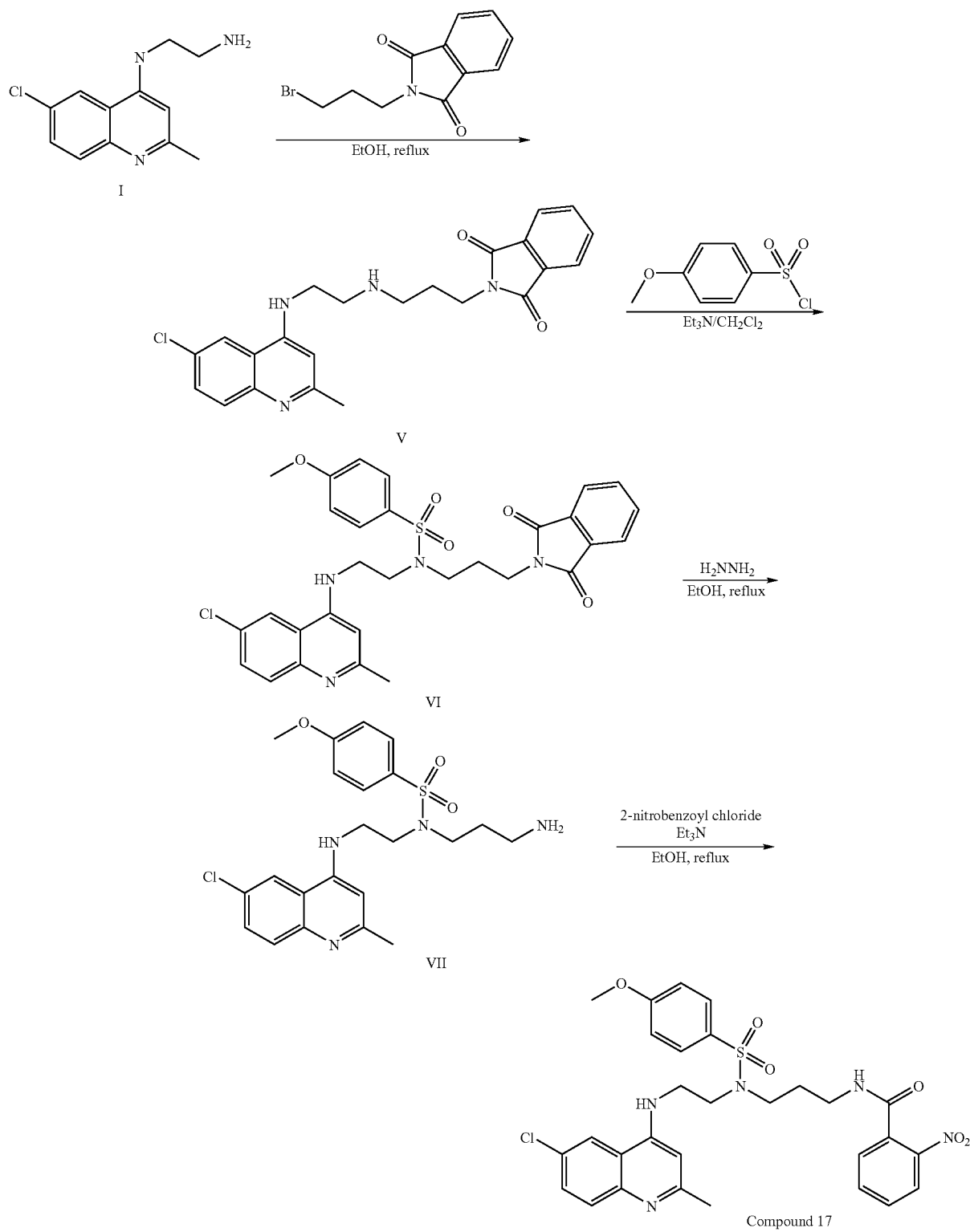

Intermediate I (1.2 g, 5.1 mmol) and N-(3-bromopropyl) phthalimide (1.64 g, 6.1 equivalents) were dissolved in ethanol (50 mL) at room temperature. The solution was kept under reflux overnight. The reaction solution was then concentrated under vacuum. A basic aqueous solution was added and the mixture thus obtained was extracted with $CH_2Cl_2$ (20 mL×2). The organic layers were combined, washed with brine, dried over $Na_2SO_4$, and concentrated to give the crude product. The crude product was purified by column chromatography over silica gel to afford intermediate V.

Intermediate VI was prepared from Intermediate V in the manner similar to that of Intermediate III described in Example 1.

Intermediate VI (450 mg, 0.76 mmol) and hydrazine hydrate (76 mg, 1.52 mmol) were added in ethanol and the mixture was refluxed for 6 hours. The crude product thus obtained was recrystallized from THF to give Intermediate VII.

An excess amount of triethylamine was added to a solution of Intermediate VII (100 mg, 0.22 mmol) and 2-nitrobenzoyl chloride (0.08 g, 0.43 mmol) in EtOH (40 mL) at room temperature during a period of 20 minutes. The reaction mixture was stirred at room temperature for 2 hours. It was then quenched with water and extracted with $CH_2Cl_2$. The organic layer was washed with brine, dried over $Na_2SO_4$, and concentrated to give a crude product. The crude product was purified by column chromatography over silica gel to afford Compound 17.

LC/MS $(M+1)^+$: 612.1.

EXAMPLE 18

Compound 18 was prepared in a manner similar to that described in Example 17.

LC/MS $(M+1)^+$: 611.1.

EXAMPLE 19

Compound 19 was prepared in a manner similar to that described in Example 1.

LC/MS $(M+1)^+$: 639.8.

EXAMPLE 20

Compound 20 was prepared in a manner similar to that described in Example 1.

LC/MS $(M+1)^+$: 694.1.

EXAMPLE 21

Compound 21 was prepared in a manner similar to that described in Example 1.

LC/MS $(M+1)^+$: 684.1.

EXAMPLE 22

Compound 22 was prepared following the procedures described below:

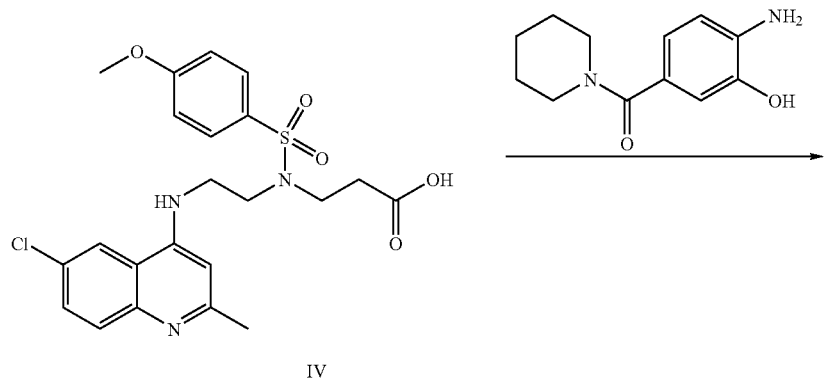

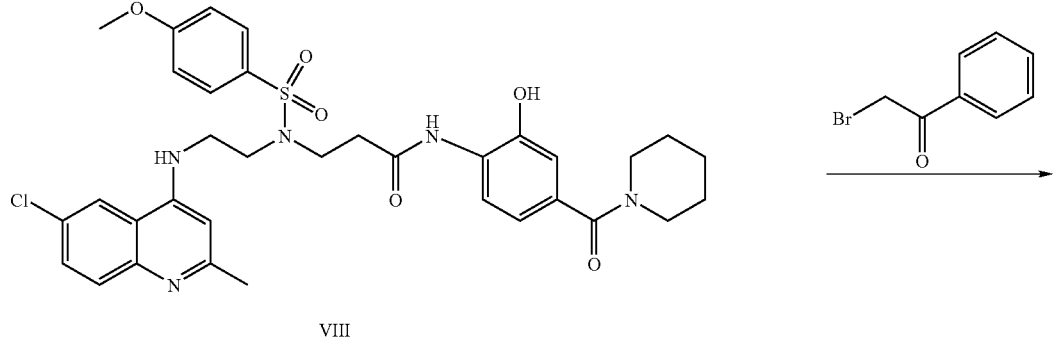

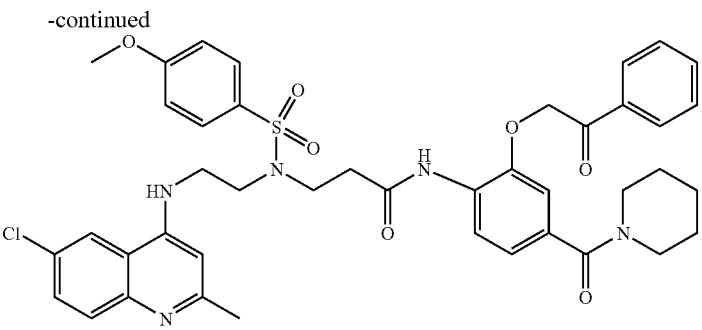

Compound 22

Intermediate VIII was prepared from Intermediate IV in the manner similar to that of Compound 1 described in Example 1.

Triethylamine (15 mL) was added dropwise to a solution of intermediate VIII (30.6 g, 100 mmol) and 4-methoxybenzenesulfonyl chloride (24.8 g, 120 mmol) in dichloromethane (220 mL) via an addition funnel over 30 minutes at 0° C. After the addition was complete, the solution was stirred for 2 hours. The reaction was then quenched with 1 N NaOH and extracted with dichloromethane. The organic extract was dried over magnesium sulfate, filtered, and concentrated under vacuum. The crude solid thus obtained was purified by re-crystallization from ethanol to afford 45.2 g of Compound 22.

LC/MS (M+1)$^+$: 798.1.

EXAMPLE 23

Compound 23 was prepared in a manner similar to that described in Example 22.
LC/MS (M+1)$^+$: 654.1.

EXAMPLE 24

Compound 24 was prepared in a manner similar to that described in Example 22.
LC/MS (M+1)$^+$: 667.8.

EXAMPLE 25

Compound 25 was prepared in a manner similar to that described in Example 22.
LC/MS (M+1)$^+$: 753.7.

EXAMPLE 26

Compound 26 was prepared in a manner similar to that described in Example 22.
LC/MS (M+1)$^+$: 705.1.

EXAMPLE 27

Compound 27 was prepared in a manner similar to that described in Example 22.
LC/MS (M+1)$^+$: 705.1.

EXAMPLE 28

Compound 28 was prepared in a manner similar to that described in Example 1.
LC/MS (M+1)$^+$: 610.1.

EXAMPLE 29

Compound 29 was prepared in a manner similar to that described in Example 1.
LC/MS (M+1)$^+$: 624.1.

EXAMPLE 30

Compound 30 was prepared in a manner similar to that described in Example 1.
LC/MS (M+1)$^+$: 724.1.

EXAMPLE 31

Compound 31 was prepared in a manner similar to that described in Example 1.
LC/MS (M+1)$^+$: 674.2.

EXAMPLE 32

Compound 32 was prepared in a manner similar to that described in Example 22.
LC/MS (M+1)$^+$: 682.1.

EXAMPLE 33

Compound 33 was prepared in a manner similar to that described in Example 22.
LC/MS (M+1)$^+$: 702.1.

EXAMPLE 34

Compound 34 was prepared in a manner similar to that described in Example 22.
LC/MS (M+1)$^+$: 686.1.

EXAMPLE 35

Compound 35 was prepared in a manner similar to that described in Example 22.
LC/MS (M+1)$^+$: 671.1.

EXAMPLE 36

Compound 36 was prepared in a manner similar to that described in Example 22.
LC/MS (M+1)$^+$: 653.1.

EXAMPLE 37

Compound 37 was prepared in a manner similar to that described in Example 22.
LC/MS (M+1)$^+$: 700.1.

EXAMPLE 38

Compound 38 was prepared in a manner similar to that described in Example 1.
LC/MS (M+1)$^+$: 694.1.

EXAMPLE 39

Compound 39 was prepared following the procedures described below:

Intermediate 1 (2.0 g, 8.51 mmol), pyridine-3-carbaldehyde (1.1 g, 8.94 mmol), NaHB(OAc)$_3$ (2.16 g, 10.21 mmol), and a catalytic amount of acetic acid were added in methanol. The mixture was stirred at room temperature overnight. The reaction was then quenched with water and the mixture was extracted with CH$_2$Cl$_2$ (50 mL×2). The organic layers were combined, washed with brine, dried over Na$_2$SO$_4$, and concentrated to give a crude product. The crude product was purified by column chromatography over silica gel using 2.5% TEA/EA as an eluant to afforded Intermediate IX.

Compound 39 was then prepared from Intermediate IX in the manner similar to that of Intermediate III described in Example 1.
LC/MS (M+1)$^+$: 497.1.

EXAMPLE 40

Compound 40 was prepared in a manner similar to that described in Example 39.
LC/MS (M+1)$^+$: 521.2.

Scheme 4

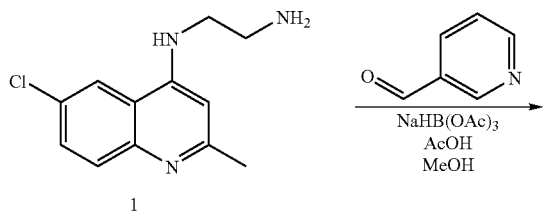

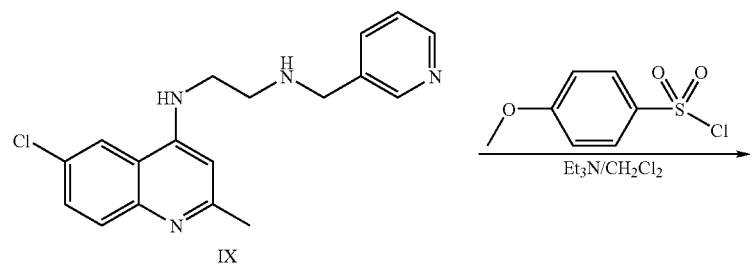

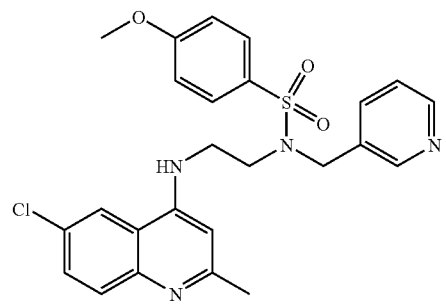

Compound 39

EXAMPLE 41

Compound 41 was prepared following the procedures described below:

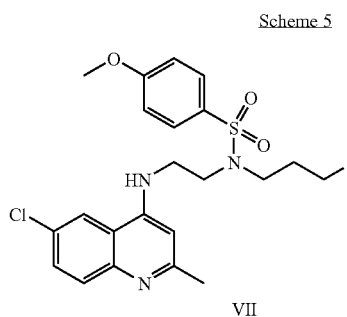

Scheme 5

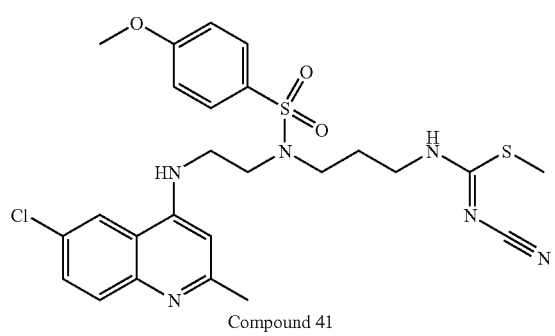

A solution of Intermediate VII (500 mg, 2.13 mmol) and N-cyanoimido-S,S-dimethyldithiocarbonate (0.62 g, 4.26 mmol) in ethanol (10 mL) was heated under microwave at 135° C. for 10 minutes. The reaction mixture was then quenched with water and extracted with $CH_2Cl_2$. The organic layer was collected, dried, and concentrated under vacuum to obtain the crude product. The crude mixture was precipitated from ether to afford Compound 41 as an off-white powder.

LC/MS $(M+1)^+$: 561.1.

EXAMPLE 42

Compound 42 was prepared following the procedures described below:

Scheme 6

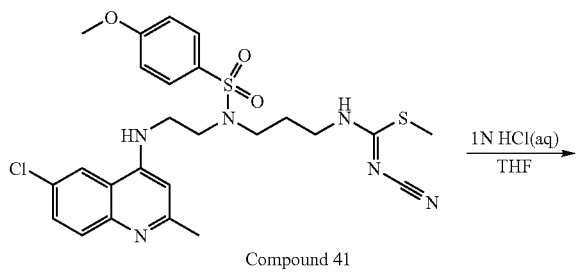

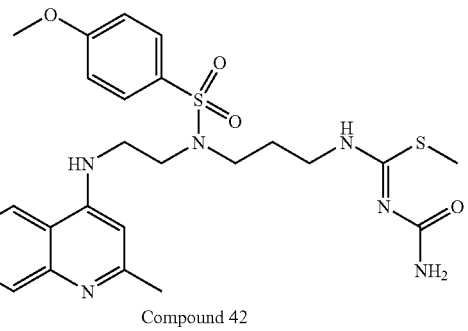

An excess amount of an 1N HCl aqueous solution was added to a solution of Compound 41 (112 mg, 0.2 mmol) in THF (10 mL). The reaction mixture was kept under reflux for 4 hours and cooled down to room temperature. Compound 42 was precipitated by addition of ethyl acetate and collected by filtration in high yield.

LC/MS $(M+1)^+$: 579.2.

EXAMPLE 43

Compound 43 was prepared in a manner similar to that described in Example 41.

LC/MS $(M+1)^+$: 481.2.

EXAMPLE 44

Compound 44 was prepared in a manner similar to that described in Example 41.

LC/MS $(M+1)^+$: 517.1.

EXAMPLE 45

Compound 45 was prepared in a manner similar to that described in Example 41.

LC/MS $(M+1)^+$: 481.1.

EXAMPLE 46

Compound 46 was prepared in a manner similar to that described in Example 41.

LC/MS $(M+1)^+$: 550.1.

EXAMPLE 47

Compound 47 was prepared in a manner similar to that described in Example 1.

LC/MS $(M+1)^+$: 748.3.

EXAMPLE 48

Compound 48 was prepared in a manner similar to that described in Example 1.

LC/MS $(M+1)^+$: 696.2.

EXAMPLE 49

Compound 57 was prepared in a manner similar to that described in Example 1.

LC/MS $(M+1)^+$: 746.2.

EXAMPLE 50

Compound 50 was prepared in a manner similar to that described in Example 1.
LC/MS (M+1)$^+$: 742.3.

EXAMPLE 51

Compound 51 was prepared in a manner similar to that described in Example 22.
LC/MS (M+1)$^+$: 750.2.

EXAMPLE 52

Compound 52 was prepared in a manner similar to that described in Example 41.
LC/MS (M+1)$^+$: 612.2.

EXAMPLE 53

Compound 53 was prepared in a manner similar to that described in Example 1.
LC/MS (M+1)$^+$: 708.2.

EXAMPLE 54

Compound 54 was prepared in a manner similar to that described in Example 1.
LC/MS (M+1)$^+$: 747.2.

EXAMPLE 55

Compound 55 was prepared in a manner similar to that described in Example 41.
LC/MS (M+1)$^+$: 606.1.

EXAMPLE 56

Compound 56 was prepared in a manner similar to that described in Example 1.
LC/MS (M+1)$^+$: 710.2.

EXAMPLE 57

Compound 57 was prepared in a manner similar to that described in Example 1.
LC/MS (M+1)$^+$: 738.2.

EXAMPLE 58

Compound 58 was prepared in a manner similar to that described in Example 1.
LC/MS (M+1)$^+$: 770.2.

EXAMPLE 59

Compound 59 was prepared in a manner similar to that described in Example 1.
LC/MS (M+1)$^+$: 708.2.

EXAMPLE 60

Compound 60 was prepared in a manner similar to that described in Example 1.
LC/MS (M+1)$^+$: 742.1.

EXAMPLE 61

Compound 61 was prepared in a manner similar to that described in Example 1.
LC/MS (M+1)$^+$: 768.3.

EXAMPLE 62

Compound 62 was prepared in a manner similar to that described in Example 1.
LC/MS (M+1)$^+$: 790.0.

EXAMPLE 63

Compound 63 was prepared in a manner similar to that described in Example 22.
LC/MS (M+1)$^+$: 703.7.

EXAMPLE 64

Compound 64 was prepared in a manner similar to that described in Example 22.
LC/MS (M+1)$^+$: 868.1.

EXAMPLE 65

Compound 65 was prepared in a manner similar to that described in Example 22.
LC/MS (M+1)$^+$: 843.2.

EXAMPLE 66

Compound 66 was prepared in a manner similar to that described in Example 1.
LC/MS (M+1)$^+$: 758.4.

EXAMPLE 67

Compound 67 was prepared in a manner similar to that described in Example 22.
LC/MS (M+1)$^+$: 828.3.

EXAMPLE 68

Compound 68 was prepared in a manner similar to that described in Example 22.
LC/MS (M+1)$^+$: 816.3.

EXAMPLE 69

Compound 69 was prepared in a manner similar to that described in Example 22.
LC/MS (M+1)$^+$: 848.3.

EXAMPLE 70

Compound 70 was prepared in a manner similar to that described in Example 1.
LC/MS (M+1)$^+$: 795.3.

EXAMPLE 71

Compound 71 was prepared in a manner similar to that described in Example 1.
LC/MS (M+1)$^+$: 684.2.

EXAMPLE 72

Compound 72 was prepared in a manner similar to that described in Example 1.
LC/MS (M+1)$^+$: 786.3.

EXAMPLE 73

Compound 73 was prepared in a manner similar to that described in Example 1.
LC/MS (M+1)$^+$: 795.4.

EXAMPLE 74

Compound 74 was prepared in a manner similar to that described in Example 22.
LC/MS (M+1)$^+$: 857.4.

EXAMPLE 75

Compound 75 was prepared in a manner similar to that described in Example 22.
LC/MS (M+1)$^+$: 888.4.

EXAMPLE 76

Compound 76 was prepared in a manner similar to that described in Example 1.
LC/MS (M+1)$^+$: 854.4.

EXAMPLE 77

Compound 77 was prepared in a manner similar to that described in Example 1.
LC/MS (M+1)$^+$: 812.4.

EXAMPLE 78

Compound 78 was prepared in a manner similar to that described in Example 1.
LC/MS (M+1)$^+$: 814.4.

EXAMPLE 79

Compound 79 was prepared in a manner similar to that described in Example 22.
LC/MS (M+1)$^+$: 832.4.

EXAMPLE 80

Compound 80 was prepared in a manner similar to that described in Example 22.
LC/MS (M+1)$^+$: 834.4.

EXAMPLE 81

Compound 81 was prepared in a manner similar to that described in Example 22.
LC/MS (M+1)$^+$: 893.3.

EXAMPLE 82

Compound 82 was prepared in a manner similar to that described in Example 22.
LC/MS (M+1)$^+$: 844.4.

EXAMPLE 83

Compound 83 was prepared in a manner similar to that described in Example 22.
LC/MS (M+1)$^+$: 883.2.

EXAMPLE 84

Compound 84 was prepared in a manner similar to that described in Example 22.
LC/MS (M+1)$^+$: 702.3.

EXAMPLE 85

Compound 85 was prepared in a manner similar to that described in Example 1.
LC/MS (M+1)$^+$: 680.2.

EXAMPLE 86

Compound 86 was prepared in a manner similar to that described in Example 1.
LC/MS (M+1)$^+$: 685.3.

EXAMPLE 87

Compound 87 was prepared in a manner similar to that described in Example 1.
LC/MS (M+1)$^+$: 747.2.

EXAMPLE 88

Compound 88 was prepared in a manner similar to that described in Example 22.
LC/MS (M+1)$^+$: 720.2.

EXAMPLE 89

Compound 89 was prepared in a manner similar to that described in Example 22.
LC/MS (M+1)$^+$: 771.1.

EXAMPLE 90

Compound 90 was prepared in a manner similar to that described in Example 1.
LC/MS (M+1)$^+$: 796.7.

EXAMPLE 91

Compounds 1-90 were tested for their efficacy in blocking activation of CXCR3 using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonists. Eu-GTP, obtained from Wallac Oy, was used in this assay to allow monitoring of agonist-dependent activation of G-protein. Stimulation of CXCR3 by interferon-α inducible protein 10 (IP-10) leads to the replacement of GDP by GTP on the α-subunit of G-protein. This GTP-Gα complex represents the activated form of G-protein. Eu-GTP, a non-hydrolysable analog of GTP, can be used to quantify the amount of activated G-protein. (Peltonen et al., Eur. J. Pharmacol. (1998) 355:275.)

Plasma membrane of CXCR3-expressing HEK293 cells was suspended in an assay buffer (50 mM NaCl, 100 μg/mL saponin, 3 mM MgCl$_2$, 3 μM GDP, 5% BSA, 50 mM HEPES, pH 7.4). An aliquot (4 μg protein) was added to each well of an AcroPlate (Pall Life Sciences, Ann Arbor, Mich.). After the addition of the test compounds (10 μM in 0.1% DMSO) and IP-10 (4 nM in the assay buffer), the assay plate was incubated in the dark at room temperature with slow shaking for 10 minutes. Eu-GTP was added to each well and the plate was incubated again for 60 minutes. The assay was terminated by washing the plate twice with a wash solution provided in the assay kit. Binding of Eu-GTP was determined based on the fluorescence signal from a Victor 2 multi-label reader.

Unexpectedly, 51 compounds showed $IC_{50}$ values lower than 1.0 μM, 22 compounds showed $IC_{50}$ values between 1 μM and 10.0 μM, and 17 compounds showed $IC_{50}$ values greater than 10.0 μM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

(I)

wherein
each of $R_1$ and $R_2$, independently, is H or $C_1$-$C_8$ alkyl; each of $R_3$ and $R_4$, independently, is H or -A-N(B)-D; at most one of $R_3$ and $R_4$ being H; and
each of $R_5$, $R_6$, $R_7$, and $R_8$, independently, is H, $C_1$-$C_8$ alkyl, or halogen;
in which A is $C_1$-$C_{12}$ alkyl optionally containing 1-6 heteroatoms; B is H or $C_1$-$C_8$ alkyl; and D is $C_1$-$C_8$ alkyl, $C_3$-$C_8$ cycloalkyl, $C_3$-$C_8$ heterocycloalkyl, aryl, heteroaryl, —C(O)$R_a$, —SO$_2$$R_a$, —C(=N—CN)—S$R_a$, —C(=N—CN)—N$R_a$$R_a$', or —C(=N—C(O)NH$_2$)—S$R_a$; or B and D together are $C_5$-$C_7$ heterocycloalkyl or heteroaryl; each of $R_a$ and $R_a$', independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl;
or a salt thereof.

2. The compound of claim 1, wherein A is $C_1$-$C_{12}$ alkylcarbonyl containing 1-6 heteroatoms and substituted with arylsulfonyl.

3. The compound of claim 2, wherein D is $C_1$-$C_8$ alkyl, heteroaryl, or aryl optionally substituted with $C_1$-$C_8$ alkyl, heteroaryl, —NO$_2$, —O$R_b$, —N($R_b$)—C(O)$R_b$', —N$R_b$$R_b$', —CO$_2$$R_b$, —C(O)—N$R_b$$R_b$', —C(O)$R_b$, —SO$_2$—N$R_b$$R_b$', or —SO$_2$$R_b$; or D and B together are $C_5$-$C_7$ heterocycloalkyl; each of $R_b$ and $R_b$', independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl.

4. The compound of claim 3, wherein the compound is one of compounds 1-16, 19-38, 47-51, 53, 54, 56-65, and 67-90.

5. The compound of claim 1, wherein A is $C_1$-$C_{12}$ alkyl optionally containing 1-6 heteroatoms and optionally substituted with arylsulfonyl.

6. The compound of claim 5, wherein D is —C(O)$R_a$, —SO$_2$$R_a$, —C(=N—CN)—S$R_a$, —C(=N—CN)—N$R_a$$R_a$', or —C(=N—C(O)NH$_2$)—S$R_a$.

7. The compound of claim 6, wherein the compound is one of compounds 17, 18, 39-46, 52, and 55.

8. A compound of formula (I):

(I)

wherein
each of $R_1$ and $R_2$, independently, is H or $C_1$-$C_8$ alkyl; or $R_1$ and $R_2$ together are cycloalkyl;
each of $R_3$ and $R_4$, independently, is H or -A-N(B)-D; at most one of $R_3$ and $R_4$ being H; and
one of $R_5$, $R_6$, $R_7$, and $R_8$ is $C_1$-$C_8$ alkyl; the other of $R_5$, $R_6$, $R_7$, and $R_8$, independtly, is H, $C_1$-$C_8$ alkyl, or halogen;
in which A is $C_1$-$C_{12}$ alkyl optionally containing 1-6 heteroatoms; B is H or $C_1$-$C_8$ alkyl; and D is $C_1$-$C_8$ alkyl, $C_3$-$C_8$ cycloalkyl, $C_3$-$C_8$ heterocycloalkyl, aryl, heteroaryl, —C(O)$R_a$, —SO$_2$$R_a$, —C(=N—CN)—S$R_a$, —C(=N—CN)—N$R_a$$R_a$', or —C(=N—C(O)NH$_2$)—S$R_a$; or B and D together are $C_5$-$C_7$ heterocycloalkyl or heteroaryl; each of $R_a$ and $R_a$', independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl;
or a salt thereof.

9. The compound of claim 8, wherein A is $C_1$-$C_{12}$ alkylcarbonyl containing 1-6 heteroatoms and substituted with arylsulfonyl.

10. The compound of claim 9, wherein D is aryl optionally substituted with —O$R_b$, or —C(O)—N$R_b$$R_b$'; each of $R_b$ and $R_b$', independently, being H, $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl.

11. The compound of claim 10, wherein the compound is compound 66.

* * * * *